(12) United States Patent
Kuwabe et al.

(10) Patent No.: US 10,576,122 B2
(45) Date of Patent: *Mar. 3, 2020

(54) METHODS OF PRODUCING ANAMORELIN HYDROCHLORIDE HAVING CONTROLLED CHLORIDE CONTENT

(71) Applicants: HELSINN HEALTHCARE SA, Lugano/Pazzallo (CH); ONO PHARMACEUTICAL CO., LTD, Osaka (JP)

(72) Inventors: Shin-itsu Kuwabe, Osaka (JP); Takehiko Yanagimachi, Osaka (JP); Hideyuki Yoshiyama, Osaka (JP); Seemon Pines, Newton, PA (US); Eleanor de Groot, Houston, TX (US); Silvina Garcia Rubio, Princeton, NJ (US); Peter Manini, Giubiasco (CH)

(73) Assignees: Helsinn Healthcare SA, Lugano/Pazzallo (CH); Ono Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/383,623

(22) Filed: Apr. 14, 2019

(65) Prior Publication Data

US 2019/0231843 A1 Aug. 1, 2019

Related U.S. Application Data

(60) Continuation of application No. 15/963,284, filed on Apr. 26, 2018, now Pat. No. 10,300,105, which is a continuation of application No. 15/135,051, filed on Apr. 21, 2016, now Pat. No. 9,981,002, which is a continuation of application No. 14/539,318, filed on Nov. 12, 2014, now Pat. No. 9,403,867, which is a division of application No. 13/865,649, filed on Apr. 18, 2013, now abandoned.

(60) Provisional application No. 61/636,108, filed on Apr. 20, 2012.

(51) Int. Cl.
| | | |
|---|---|---|
| C07D 401/06 | (2006.01) | |
| A61K 31/454 | (2006.01) | |
| A61K 38/05 | (2006.01) | |
| C07D 401/12 | (2006.01) | |
| C07K 5/062 | (2006.01) | |
| A61K 9/16 | (2006.01) | |

(52) U.S. Cl.
CPC ............ *A61K 38/05* (2013.01); *A61K 9/1682* (2013.01); *C07D 401/06* (2013.01); *C07D 401/12* (2013.01); *C07K 5/06034* (2013.01)

(58) Field of Classification Search
CPC .............. C07D 401/06; A61K 31/454
USPC ........................................ 546/201; 514/323
See application file for complete search history.

(56) References Cited

U.S. PATENT DOCUMENTS

| | | | |
|---|---|---|---|
| 6,576,648 B2 | 6/2003 | Ankersen et al. | |
| 7,825,138 B2 | 11/2010 | Lorimer et al. | |
| 8,673,947 B2 | 3/2014 | Polvino et al. | |
| 9,403,867 B2 | 8/2016 | Kuwabe et al. | |
| 9,872,883 B2 * | 1/2018 | Kuwabe ............... | C07D 401/06 |
| 9,956,261 B2 * | 5/2018 | Kuwabe ............... | C07D 401/06 |
| 9,981,002 B2 * | 5/2018 | Kuwabe ............... | C07D 401/06 |
| 2014/0018391 A1 | 1/2014 | Kuwabe et al. | |
| 2016/0229889 A1 | 8/2016 | Kuwabe et al. | |
| 2016/0235804 A1 | 8/2016 | Kuwabe et al. | |
| 2016/0237115 A1 | 8/2016 | Kuwabe et al. | |

FOREIGN PATENT DOCUMENTS

| | | |
|---|---|---|
| CN | 103857669 A1 | 6/2014 |
| EP | 2838892 A1 | 2/2015 |
| WO | 2001034593 A1 | 5/2001 |
| WO | 2005030698 A1 | 4/2005 |
| WO | 2008100448 A2 | 8/2008 |
| WO | 2010099522 A1 | 9/2010 |
| WO | 2013158874 A1 | 10/2013 |

OTHER PUBLICATIONS

Stahl "Handbook of Pharmaceutical Salts: Properties Selection and Use" Verlag Helvetica Chi mica Acta: 2002, pp. 250-253.
Written Opinion and International Search Report, dated Aug. 6, 2013, which issued during the prosecution of International Patent Application No. PCTIUS2013/037159 which corresponds to the present application.
Parts per Million conversions, Delloy's Labb Tech Res. p. 1-5 (2000).
FDA "Guidance of industry Q3B . . . " p. 1-18 (2006).
Q11 FDA p. 1-36 (2012).
Q3A FDA p. 1-17 (2008).
Q3C FDA p. 1-16 (1997).
Q3C—tables & list, p. 1-1 0 (2012).
Seddon "Pseudopolymorph . . . " Crystal growth and design v94)1087 (2004).
Bari et al. "Impurity profile . . . " Eur. J. anal. Chem. vp;/ 2(1) p. 32-53(2007).
Hu&Liu "Qulitay control. . . . " p. 183-21 0 Wide spectra of quality control (2011).
Witschi et al. "Residual solvents . . . " Eur. J. Pharma. Biopharmaceutics 43, p. 215-242 (1997).
Anamorelin HCI, MCE, p. 1 (2016).
ONO—pharmaceutical Co. p. 1-3 (2011).
Spray drying "European conference" p. 1-6 (2007).
Rousseau "Handbook of . . . " p. 762-763 (1987).
Berge et al. "Pharmaceutical salts" J. Phar. Sci 66(1) 1-19 (1977).
Polvino "Enhanced migrain . . . "CA153:351081 (2010).

(Continued)

*Primary Examiner* — Charanjit Aulakh
(74) *Attorney, Agent, or Firm* — Clark G. Sullivan

(57) ABSTRACT

The present invention relates to particulate forms of anamorelin monohydrochloride or a composition comprising anamorelin monohydrochloride having controlled chloride content, preferably isolated in an amorphous and/or fine particulate state, processes for making the particulate forms, and pharmaceutical compositions comprising the particulate forms.

25 Claims, 1 Drawing Sheet

(56) References Cited

OTHER PUBLICATIONS

International Preliminary Report on Patentability issued in PCT/US2013/037159 dated Apr. 24, 2014.
Paul, Bernhard, et al "A Practical Synthesis of the Pseudotripeptide RC-1291." (2006) Organic Process Research & Development v.10, p. 339-345.

* cited by examiner

METHODS OF PRODUCING ANAMORELIN HYDROCHLORIDE HAVING CONTROLLED CHLORIDE CONTENT

FIELD OF THE INVENTION

The present invention relates to anamorelin hydrochloride, improved forms of anamorelin hydrochloride having reduced impurities and controlled chloride content, and improved processes for making and using anamorelin hydrochloride.

BACKGROUND OF THE INVENTION

Growth hormone is a major participant in the control of several complex physiologic processes including growth and metabolism. Growth hormone is known to have a number of effects on metabolic processes such as stimulating protein synthesis and mobilizing free fatty acids, and causing a switch in energy metabolism from carbohydrate to fatty acid metabolism. Deficiencies in growth hormone can result in dwarfism and other severe medical disorders.

The release of growth hormone from the pituitary gland is controlled directly and indirectly by a number of hormones and neurotransmitters. Growth hormone release can be stimulated by growth hormone releasing hormone (GHRH) and inhibited by somatostatin.

The use of certain compounds to increase levels of growth hormone in mammals has previously been proposed. Anamorelin is one such compound. Anamorelin is a synthetic orally active compound originally synthesized in the 1990s as a growth hormone secretagogue for the treatment of cancer related cachexia. The free base of anamorelin is chemically defined as:

(3R) 1-(2-methylalanyl-D-tryptophyl)-3-(phenylmethyl)-3-piperidinecarboxylic acid 1,2,2trimethylhydrazide, 3-{(2R)-3-{(3R)-3-benzyl-3-[(trimethylhydrazino)carbonyl]piperidin-1-yl}-2-[(2-met hylalanyl)amino]-3-oxopropyl}-1H-indole, or 2-Amino-N-[(1R)-2-[(3R)-3-benzyl-3-(N,N',N'-trimethylhydrazino-carbonyl)piperidin-1-yl]-1-(1H-indol-3-ylmethyl)-2-oxoethyl]-2-methylpropionamide and has the below chemical structure:

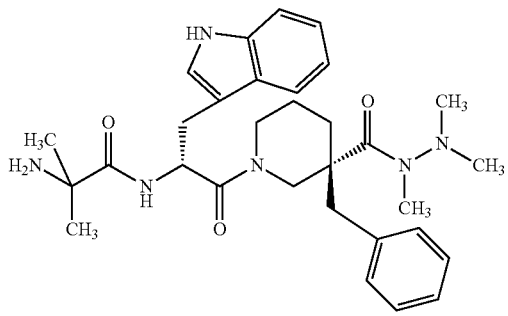 [SMILES: CN(C)N(C)C(=O)[C@@]1(Cc2ccccc2)CCCN(C(=O)[C@@H](Cc2c[nH]c3ccccc23)NC(=O)C(C)(C)N)C1]

U.S. Pat. No. 6,576,648 to Ankerson reports a process of preparing anamorelin as the fumarate salt, with the hydrochloride salt produced as an intermediate in Step (j) of Example 1. U.S. Pat. No. 7,825,138 to Lorimer describes a process for preparing crystal forms of the free base of anamorelin.

There is a need to develop anamorelin monohydrochloride as an active pharmaceutical ingredient with reduced impurities and improved stability over prior art forms of anamorelin hydrochloride, such as those described in U.S. Pat. No. 6,576,648, having good solubility, bioavailability and processability. There is also a need to develop methods of producing pharmaceutically acceptable forms of anamorelin monohydrochloride that have improved yield over prior art processes, reduced residual solvents, and controlled distribution of chloride content.

SUMMARY OF THE INVENTION

It has unexpectedly been discovered that the process of making the hydrochloride salt of anamorelin described in Step (j) of U.S. Pat. No. 6,576,648 can result in excessive levels of chloride in the final product, and that this excess chloride leads to the long-term instability of the final product due at least partially to an increase in the amount of the less stable dihydrochloride salt of anamorelin. Conversely, because anamorelin free base is less soluble in water than the hydrochloride salt, deficient chloride content in the final product can lead to decreased solubility of the molecule. The process described in U.S. Pat. No. 6,576,648 also yields a final product that contains more than 5000 ppm (0.5%) of residual solvents, which renders the product less desirable from a pharmaceutical standpoint, as described in ICH Harmonized Tripartite Guideline. See Impurities: Guideline for residual solvents Q3C(R3).

In order to overcome these problems, methods have been developed which, for the first time, allow for the efficient and precise control of the reaction between anamorelin free base and hydrochloric acid in situ, thereby increasing the yield of anamorelin monohydrochloride from the reaction and reducing the incidence of unwanted anamorelin dihydrochloride. According to the method, the free base of anamorelin is dissolved in an organic solvent and combined with water and hydrochloric acid, with the molar ratio of anamorelin and chloride tightly controlled to prevent an excess of chloride in the final product. The water and hydrochloric acid can be added either sequentially or at the same time as long as two separate phases are formed. Without wishing to be bound by any theory, it is believed that as the anamorelin free base in the organic phase is protonated by the hydrochloric acid it migrates into the aqueous phase. The controlled ratio of anamorelin free base and hydrochloric acid and homogenous distribution in the aqueous phase allows for the controlled formation of the monohydrochloride salt over the dihydrochloride, and the controlled distribution of the resulting chloride levels within individual batches and among multiple batches of anamorelin monohydrochloride.

Thus, in a first embodiment the invention provides methods for preparing anamorelin monohydrochloride or a composition comprising anamorelin monohydrochloride comprising: (a) dissolving anamorelin free base in an organic solvent to form a solution; (b) mixing said solution with water and hydrochloric acid for a time sufficient to: (i) react said anamorelin free base with said hydrochloric acid, and (ii) form an organic phase and an aqueous phase; (c) separating the aqueous phase from the organic phase; and (d) isolating anamorelin monohydrochloride from the aqueous phase.

In a particularly preferred embodiment, the molar ratio of anamorelin to hydrochloric acid used in the process is less than or equal to 1:1, so as to reduce the production of anamorelin dihydrochloride and other unwanted chemical species. Thus, for example, hydrochloric acid can be added at a molar ratio of from 0.90 to 1.0 relative to said anamorelin, from 0.90 to 0.99, or from 0.93 to 0.97.

In another particularly preferred embodiment, the anamorelin monohydrochloride or a composition comprising anamorelin monohydrochloride is isolated from the aqueous phase via spray drying, preferably preceded by distillation. This technique has proven especially useful in the manufacture of anamorelin monohydrochloride or a composition comprising anamorelin monohydrochloride because of the excellent reduction in solvent levels observed, and the production of a stable amorphous form of anamorelin monohydrochloride or a composition comprising anamorelin monohydrochloride.

In other embodiments, the invention relates to the various forms of anamorelin monohydrochloride and compositions comprising anamorelin monohydrochloride produced by the methods of the present invention. In a first embodiment, which derives from the controlled chloride content among batches accomplished by the present methods, the invention provides anamorelin monohydrochloride or a composition comprising anamorelin monohydrochloride having an interbatch chloride content of from 5.8 to 6.2%, preferably from 5.8 to less than 6.2%. Alternatively, the invention provides anamorelin monohydrochloride or a composition comprising anamorelin monohydrochloride having a molar ratio of chloride to anamorelin less than or equal to 1:1, such as from 0.9 to 1.0 or 0.99. In yet another embodiment the invention provides an amorphous form of anamorelin monohydrochloride or a composition comprising anamorelin monohydrochloride. Further descriptions of the anamorelin monohydrochloride and compositions comprising the anamorelin monohydrochloride are given in the detailed description which follows.

Additional embodiments and advantages of the invention will be set forth in part in the description which follows, and in part will be obvious from the description, or may be learned by practice of the invention. The embodiments and advantages of the invention will be realized and attained by means of the elements and combinations particularly pointed out in the appended claims. It is to be understood that both the foregoing general description and the following detailed description are exemplary and explanatory only and are not restrictive of the invention, as claimed.

That is, the present invention relates to:

[Par. 1] Anamorelin monohydrochloride having a chloride content ranging from 5.8 to 6.2%.

[Par. 2] Anamorelin monohydrochloride comprising a chloride:anamorelin molar ratio of from 0.9 to 0.99.

[Par. 3] Anamorelin monohydrochloride in an amorphous state.

[Par. 4] The anamorelin monohydrochloride of Par. 1, 2 or 3, in an isolated state.

[Par. 5] The anamorelin monohydrochloride of Par. 1, 2 or 3, comprising less than 0.5% impurities.

[Par. 6] The anamorelin monohydrochloride of Par. 1, 2 or 3, comprising from 1 to 3% water.

[Par. 7] The anamorelin monohydrochloride of Par. 5, wherein the impurities are selected from by-products, contaminants, degradation products and residual solvents.

[Par. 8] The anamorelin monohydrochloride of Par. 7, comprising a residual solvent selected from methanol, butyl acetate, propyl acetate, ethyl acetate, isopropyl acetate, isobutyl acetate, methyl acetate, methylethyl ketone, methylisobutyl ketone, 2-methyltetrahydrofuran and combinations thereof in an amount less than 1000 ppm.

[Par. 9] The anamorelin monohydrochloride of Par. 8, wherein the residual solvent is isopropyl acetate.

[Par. 10] The anamorelin monohydrochloride of Par. 1, 2 or 3, having a purity greater than 99%.

[Par. 11] Anamorelin monohydrochloride having a purity greater than 99% and a chloride content of from 5.8 to 6.2%, comprising less than 0.5% residual solvent.

[Par. 12] A composition comprising anamorelin monohydrochloride, wherein the composition comprises a chloride content of from 5.8 to 6.2%.

[Par. 13] A composition comprising anamorelin monohydrochloride wherein the composition comprises a chloride:anamorelin molar ratio of from 0.9 to 0.99.

[Par. 14] The composition of Par. 12 or 13, in the substantial absence of anamorelin hydrochloride other than anamorelin monohydrochloride.

[Par. 15] The composition of Par. 12, 13 or 14, in an amorphous state.

[Par. 16] The composition of Par. 12, 13, 14 or 15, in an isolated state.

[Par. 17] The composition of Par. 12, 13, 14 or 15, comprising less than 0.5% impurities.

[Par. 18] The composition of Par. 12, 13, 14 or 15, comprising from 1 to 3% water.

[Par. 19] The composition of Par. 17, wherein the impurities are selected from by-products, contaminants, degradation products and residual solvents.

[Par. 20] The composition of Par. 19, comprising a residual solvent selected from methanol, butyl acetate, propyl acetate, ethyl acetate, isopropyl acetate, isobutyl acetate, methyl acetate, methylethyl ketone, methylisobutyl ketone, 2-methyltetrahydrofuran and combinations thereof in an amount less than 1000 ppm.

[Par. 21] A composition comprising anamorelin monohydrochloride in the substantial absence of anamorelin hydrochloride other than anamorelin monohydrochloride, having a chloride content of from 5.8 to 6.2%, less than 0.5% residual solvent, and a purity greater than 99%.

[Par. 22] A process for preparing anamorelin monohydrochloride comprising:
  a) dissolving anamorelin free base in an organic solvent to form a solution;
  b) mixing said solution with water and hydrochloric acid for a time sufficient to:
    i) react said anamorelin free base with said hydrochloric acid, and
    ii) form an organic phase and an aqueous phase;
  c) separating the aqueous phase from the organic phase; and
  d) isolating said anamorelin monohydrochloride from said aqueous phase.

[Par. 23] The process of Par. 22, wherein said water and hydrochloric acid in step b are added sequentially or concurrently to said solution.

[Par. 24] The process of Par. 23, wherein said organic solvent is selected from butyl acetate, propyl acetate, ethyl acetate, isopropyl acetate, isobutyl acetate, methyl acetate, methylethyl ketone, methylisobutyl ketone, 2-methyltetrahydrofuran, and combinations thereof.

[Par. 25] The process of Par. 24, wherein said organic solvent is isopropyl acetate.

[Par. 26] The process of Par. 22, wherein the anamorelin monohydrochloride is isolated from said aqueous phase by spray drying.

[Par. 27] The process of Par. 22, wherein said anamorelin monohydrochloride is combined with from 0.9 to 1.0 molar equivalents of hydrochloric acid.

[Par. 28] The process of Par. 22, further comprising processing the anamorelin monohydrochloride into a finished dosage form.

[Par. 29] Anamorelin monohydrochloride produced by the method of Par. 22.

[Par. 30] A pharmaceutical composition comprising:
   a) a therapeutically effective amount of the anamorelin monohydrochloride of Par. 1, 2, 3 or 29, or the composition of Par. 12; and
   b) one or more pharmaceutically acceptable excipients.

[Par. 31] A method of making a pharmaceutical dosage form comprising:
   a) combining a therapeutically effective amount of the anamorelin monohydrochloride of Par. 1, 2, 3, or 29, or the composition of Par. 12, with one or more pharmaceutically acceptable excipients to form a mixture; and
   b) processing said mixture into a finished dosage form.

Additional embodiments and advantages of the invention will be set forth in part in the description which follows, and in part will be obvious from the description, or may be learned by practice of the invention. The embodiments and advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

Figure 1:
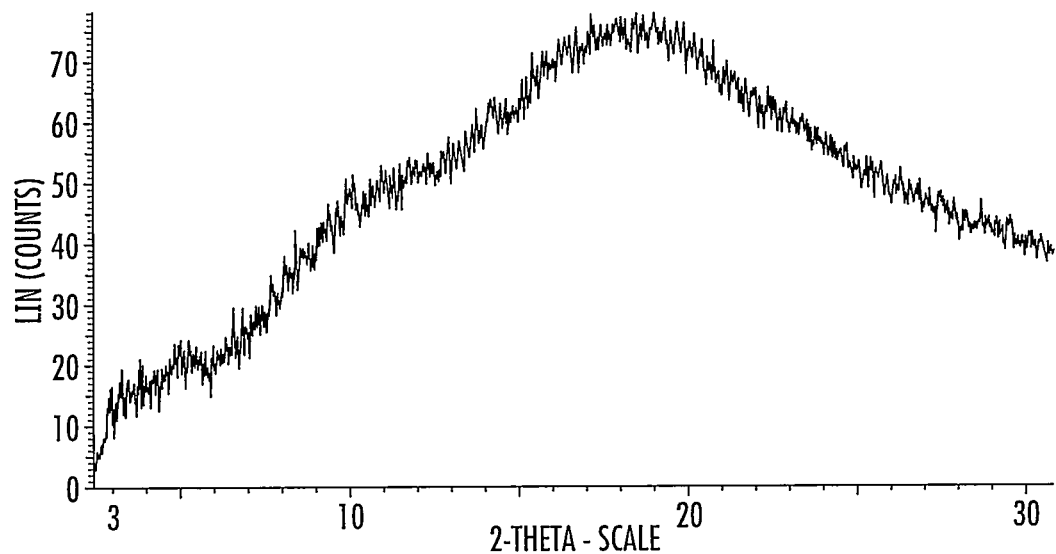
FIG. 1 is an X-ray powder diffraction pattern of amorphous anamorelin monohydrochloride or a composition comprising amorphous anamorelin monohydrochloride prepared according to the methods of the present invention.

The present invention may be understood more readily by reference to the following detailed description of preferred embodiments of the invention and the Examples included therein.

Definitions and Use of Terms

"A," "an" and "the" include plural referents unless the context clearly dictates otherwise. Thus, for example, reference to "an ingredient" includes mixtures of ingredients, reference to "an active pharmaceutical agent" includes more than one active pharmaceutical agent, and the like.

"Comprise," or variations such as "comprises" or "comprising," will be understood to imply the inclusion of a stated element, integer or step, or group of elements, integers or steps, but not the exclusion of any other element, integer or step, or group of elements, integers or steps.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

All percentages and parts (i.e. ppm) expressed herein are stated on a weight basis unless specifically stated otherwise.

Unless otherwise specified herein, it will be understood that all numeric values and ranges could be qualified by the term "about" or "approximately" to accommodate the degree of imprecision or variability allowed in the pharmaceutical industry for manufacturing imprecision, degradation over time, and generic equivalence. Unless otherwise indicated, variability of +/10% is allowed and intended for any numeric figure or range given in this application, and is meant by the term "about" or "approximately."

"Impurity" refers to any chemical in a pharmaceutical ingredient other than anamorelin monohydrochloride as the ingredient itself and water. Impurities thus include reaction by-products, contaminants, degradation products, and residual solvents such as organic volatile impurities.

"Residual solvent" refers to any organic solvent which is used in preparing anamorelin monohydrochloride.

"Isolated" refers to a state suitable for use as an active pharmaceutical ingredient in solid form, prior to admixing with any pharmaceutically acceptable excipients. Thus, the term generally requires that the recited ingredient be present as an isolated solid material to the exclusion of any pharmaceutically acceptable excipients, and preferably having less than 10, 5, 3, 1, or 0.5% impurities.

"Anamorelin monohydrochloride" refers to the salt form of anamorelin comprising a precise 1:1 stoichiometric ratio of anamorelin and HCl (i.e. 6.08 wt % Cl—). However, the anamorelin monohydrochloride may be present within a composition that does not have a precise 1:1 ratio of anamorelin and HCl because, for example, the composition may contain small quantities of anamorelin free base and/or anamorelin hydrochloride (e.g., anamorelin dihydrochloride) other than anamorelin monohydrochloride which do not substantially affect the stability of the composition. Thus, expressed as a weight percentage of chloride content, "anamorelin monohydrochloride" or "a composition comprising anamorelin monohydrochloride" may comprise from 5.6 to 6.3 wt %, and preferably from 5.8 to 6.2 wt %, more preferably from 5.9 or 6.0 to 6.1 wt % chloride. The chloride content in the composition is calculated by the formula described in the Example 1. The "hydrochloride" salt of anamorelin, in contrast, encompasses any molar ratio of anamorelin to HCl. "Anamorelin" is used herein to refer to the hydrochloride salt of anamorelin as well as the free base, and should not be taken to mean the free base unless stated so expressly.

"A composition comprising anamorelin monohydrochloride" refers to the active pharmaceutical ingredient which comprises anamorelin monohydrochloride and does not include any pharmaceutically acceptable excipients. More concretely the term refers to the composition having a chloride content ranging from 5.8 to 6.2%, preferably from 5.8 to 6.1%, in the substantial absence of anamorelin free base, anamorelin hydrochloride other than anamorelin monohydrochloride, and without any pharmaceutically acceptable excipients.

"Purity" refers to the converted value into anamorelin free base within the sample when anamorelin monohydrochloride or a composition comprising anamorelin monohydrochloride prepared by the methods of present invention is measured via HPLC under the conditions described in Example 3.

Methods of Production

As discussed above, the present invention provides methods of producing high-quality anamorelin monohydrochloride as an active pharmaceutical ingredient, as well as the product produced by such methods. The anamorelin hydrochloride of the present invention is preferably referred to simply as anamorelin hydrochloride, but could also be considered a composition comprising anamorelin monohydrochloride, due to the presence of impurities and degradation products.

Thus, in one embodiment the present invention provides methods for preparing anamorelin monohydrochloride or a composition comprising anamorelin monohydrochloride having a controlled content and distribution of chloride comprising: (a) dissolving anamorelin free base in an organic solvent to form a solution; (b) mixing said solution with water and hydrochloric acid for a time sufficient to: (i) react said anamorelin free base with said hydrochloric acid; and (ii) form an organic phase and an aqueous phase; (c) separating the aqueous phase from the organic phase; and (d) isolating anamorelin monohydrochloride from the aqueous phase.

The organic solvent used to prepare the initial solution is preferably one in which (i) anamorelin free base is more soluble than it is in water (ii) anamorelin monohydrochloride is less soluble than it is in water, (iii) the organic solvent has limited miscibility with water, and (iv) the organic solvent forms an azeotrope with water or has a lower boiling point than water.

Examples of suitable organic solvents for the anamorelin free base include but are not limited to butyl acetate, propyl acetate, ethyl acetate, isopropyl acetate, isobutyl acetate, methyl acetate, methylethyl ketone, methylisobutyl ketone and 2-methyltetrahydrofuran, preferably isopropyl acetate.

The concentration of the hydrochloric acid solution is governed primarily by the desired molar ratio of anamorelin and chloride in the final composition, which will dictate the number of moles of hydrochloric acid in the aqueous phase. In a preferred embodiment, the molarity of the hydrochloric acid solution ranges from about 0.1 to about 13 or from about 1.0 to about 10, and the volume of the solution is determined by the molarity of the solution and the quantity of anamorelin to be reacted. In various embodiments, the molar ratio of chloride to anamorelin free base in the reaction vessel can range from about 0.85 to about 1.04, from about 0.92 to about 1.02, from about 0.92 to about 1.00, or from about 0.93 to about 0.97.

Once the anamorelin with hydrochloric acid reaction is complete, the organic phase can be separated from the aqueous phase by any suitable phase extraction technique, including physical extraction of one phase from the mixture or distillation. Distillation can be performed using various means, such as simple distillation, fractional distillation, vacuum distillation and preferably azeotropic distillation. The distillation temperature is determined based upon the boiling point of the particular organic solvent(s) intended to be removed.

Once the aqueous phase has been separated from the organic phase, the anamorelin monohydrochloride or a composition comprising anamorelin monohydrochloride can be isolated from the aqueous phase via known techniques, including settling, sedimentation and concentration. Concentration is the preferred method, particularly concentration via spray drying, optionally in the presence of an inert gas.

Spray drying is a method of producing a dry powder from a liquid or slurry by rapidly drying with a hot gas. It is well suited for the continuous production of dry solids in either powder, granulate or agglomerate form from liquid feedstocks as solutions, emulsions and pumpable suspensions. Spray drying is an ideal process where the end-product must comply with precise quality standards regarding particle size distribution, residual moisture content, bulk density, and/or particle shape.

Spray drying involves the atomization of a liquid feedstock into a droplet spray, and contacting the droplets with hot air in a drying chamber. The spray is produced by either a rotary (wheel) or nozzle atomizer. Evaporation of moisture from the droplets and formation of dry particles proceed under controlled temperature and airflow conditions. Powder is discharged continuously from the drying chamber. Operating conditions and dryer design are selected according to the drying characteristics of the product and powder specifications.

A spray dryer is a device used in spray drying. It takes a liquid stream and separates the solute or suspension from a liquid phase by evaporating the solvent. The solid is usually collected in a drum or cyclone. The liquid input stream is sprayed through a nozzle into a hot vapor stream and vaporized. Solids form as moisture quickly leaves the droplets. A nozzle is usually used to make the droplets as small as possible, maximizing heat transfer and the rate of water vaporization. A representative spray dryer comprises a feed pump, atomizer, air heater, air disperser, drying chamber, and systems for exhaust air cleaning and powder recovery. The selection of the atomizer, the most suitable airflow pattern, and the drying chamber design are determined by the drying characteristics and quality requirements for the particular product.

The initial contact between spray droplets and drying air controls evaporation rates and product temperatures in the dryer. There are three modes of contact: 1) Co-current: Drying air and particles move through the drying chamber in the same direction; 2) Counter-current: Drying air and particles move through the drying chamber in opposite directions; and 3) Mixed flow: Particle movement through the drying chamber experiences both co-current and counter-current phases.

Many commercially available spray dryers can be used in the spray drying step according to the present invention. A representative example is the Mini-Spray Dryer (Model: Buchi 190, Switzerland), which operates in a co-current manner, i.e., the sprayed product and the drying gas flow in the same direction. Other suitable spray dryers include the Niro Mobile Minor (trade mark, GEA Process Engineering Inc.), Niro QSD-3.6 (trade mark, GEA Process Engineering Inc.), L-8i (Ohkawara Kakoki Co., Ltd.) and so forth. The drying gas can be air or inert gases such as nitrogen, argon and carbon dioxide. The spray drying is preferably carried out with the inlet gas temperature in the range of from about 180 to about 200° C. and the outlet gas temperature in the range of from about 80 to about 100° C. Preferred methods of spray drying the anamorelin hydrochloride are given in the examples hereto.

Anamorelin Monohydrochloride

Still other embodiments pertain to the novel forms of anamorelin monohydrochloride or compositions comprising anamorelin monohydrochloride produced by the present invention. For example, in a first principal embodiment, the invention provides for anamorelin monohydrochloride or compositions comprising anamorelin monohydrochloride having a uniformly controlled chloride content among batches. In this embodiment the invention provides anamorelin monohydrochloride having an inter-batch (i.e. batch-to-batch) chloride content that varies by no more than 7%, 5%, 3% or even 2%. For example, the invention may provide anamorelin monohydrochloride or a composition comprising anamorelin monohydrochloride having an inter-batch chloride content that ranges from 5.8 to 6.2%, 5.9 to 6.2%, 5.9 to 6.1%, or 6.0 to 6.1%.

In a second principal embodiment, the invention provides anamorelin monohydrochloride or a composition comprising anamorelin monohydrochloride having a molar ratio of chloride to anamorelin of from 0.92 to 1.02, or from 0.95 to 1.00. This ratio can exist throughout an entire batch, as an average of samples taken from the batch, or as one or more samples within a batch.

A third principal embodiment provides anamorelin monohydrochloride or a composition comprising anamorelin monohydrochloride in an amorphous state. The amorphous state can be represented by an X-ray powder diffraction pattern substantially as depicted in FIG. 1 or, alternatively or in addition, by the infrared resonance spectrum depicted in FIG. 2.

The anamorelin monohydrochloride or a composition comprising anamorelin monohydrochloride of each of the foregoing principal embodiments is preferably highly soluble in water. For example, the solubility in water of the anamorelin monohydrochloride or a composition comprising anamorelin monohydrochloride is preferably greater than about 100 mg/ml. The anamorelin monohydrochloride or composition comprising anamorelin monohydrochloride also preferably has a low residual solvent content. For example, the total organic volatile impurities such as methanol, isopropanol, isopropyl acetate, ethyl acetate or other organic solvents used in preparing the drug substance are preferably less than 5,000 ppm, 3,000 ppm, or even 1,000 ppm. Alternatively or in addition, the anamorelin monohydrochloride or composition comprising anamorelin monohydrochloride has a residual solvent content less than about 0.5%, 0.3%, or even 0.1% based upon the total weight of the anamorelin monohydrochloride or composition comprising anamorelin monohydrochloride.

The anamorelin monohydrochloride or composition comprising anamorelin monohydrochloride of each of the foregoing embodiments preferably has high purity and low impurities including residual solvents. For example, total impurities such as by-products, contaminants, degradation products and residual solvents used in preparing the drug substance are preferably less than 3%, 2%, 1%, or 0.5%. In other words, the anamorelin monohydrochloride or composition comprising anamorelin monohydrochloride is in a pharmaceutically acceptable form having greater than 97%, 98%, or even 99% purity.

Alternatively or in addition, the anamorelin monohydrochloride or composition comprising anamorelin monohydrochloride of each of the foregoing embodiments can be characterized by the weight percent of chloride in the composition, or in a sample of the composition, and in various embodiments the anamorelin monohydrochloride or composition comprising anamorelin monohydrochloride is defined by a chloride content ranging from about 5.8% to about 6.2%, and preferably from about 5.9% to about 6.1% (or 6.08%). The anamorelin monohydrochloride or composition comprising anamorelin monohydrochloride can also be characterized by its water content, alternatively or in addition to the other characteristics of the compound, and in various embodiments the compounds of the present invention comprise less than 5, 4, 3 or 2% water.

Medical Uses

Because the anamorelin monohydrochloride or composition comprising anamorelin monohydrochloride of the present invention has growth hormone secretagogue activity, it is useful for preventing and/or treating conditions which require increased plasma growth hormone levels, as in growth hormone deficient humans, elderly patients and livestock. The anamorelin monohydrochloride or a composition comprising anamorelin monohydrochloride is found particularly useful in the treatment of cancer related cachexia.

Pharmaceutical Dosage Forms

The anamorelin monohydrochloride or composition comprising anamorelin monohydrochloride of the present invention can be present in an isolated state or, alternatively, it can be formulated into a pharmaceutical dosage form (i.e., pharmaceutical composition) that comprises a therapeutically effective amount of the compound and one or more pharmaceutically acceptable excipients. As used herein the language "pharmaceutically acceptable excipient" includes solvents, dispersion media, coatings, antibacterial and antifungal agents, tonicity agents, buffers, antioxidants, preservatives, absorption delaying agents, and the like, compatible with pharmaceutical administration.

The pharmaceutical compositions can be included in a container, pack, or dispenser together with instructions for administration.

A pharmaceutical composition is formulated to be compatible with its intended route of administration. Examples of routes of administration include parenteral, oral, transmucosal, and rectal administration. The compounds for use in the method of the invention can be formulated for administration by any suitable route, such as for oral or parenteral, for example, transmucosal (e.g., sublingual, lingual, (trans)buccal, nasal, (trans)dermal, and (trans)rectal) administration.

Suitable compositions and dosage forms include tablets, capsules, caplets, pills, gel caps, troches, dispersions, suspensions, solutions, syrups, granules, beads, gels, powders, pellets, magmas, lozenges, discs, suppositories, liquid sprays, or dry powders.

It is preferred that the anamorelin monohydrochloride or the composition comprising anamorelin monohydrochloride be orally administered. Suitable oral dosage forms include, for example, tablets, capsules or caplets prepared by conventional means with pharmaceutically acceptable excipients such as binding agents (e.g., polyvinylpyrrolidone or hydroxypropylmethylcellulose); fillers (e.g., lactose, microcrystalline cellulose or calcium phosphate); lubricants (e.g., magnesium stearate, talc or silica); disintegrants (e.g., sodium starch glycolate); and/or wetting agents (e.g., sodium lauryl sulfate). If desired, the tablets can be coated, e.g., to provide for ease of swallowing or to provide a delayed release of active ingredients, using suitable methods. Tablets are typically formed by compression methods, whereas capsules are formed by filling a dry admixture into a hard outer shell.

Liquid preparations can be in the form of solutions, syrups or suspensions, and are prepared by mixing the excipients along with the anamorelin hydrochloride in a suitable liquid medium such as water or alcohol. Liquid preparations (e.g., solutions, suspensions and syrups) suitable for oral administration can be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl hydroxy benzoates or sorbic acid).

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1. Preparation of Anamorelin Hydrochloride

Various methods have been developed to prepare the hydrochloric acid salt of anamorelin, with differing results.

In a first method, which is the preferred method of the present invention, anamorelin free base was carefully measured and dissolved in isopropyl acetate. Anamorelin free base was prepared according to known method (e.g., U.S. Pat. No. 6,576,648). A fixed volume of HCl in water containing various molar ratios (0.80, 0.95, 1.00 or 1.05) of HCl relative to the anamorelin free base was then combined with the anamorelin/isopropyl acetate solution, to form a mixture having an organic and an aqueous phase. The aqueous phase of the mixture was separated from the organic phase and the resulting aqueous phase was concentrated by spray drying to obtain the batches of anamorelin monohydrochloride (or a composition comprising anamorelin monohydrochloride) shown in Table 1A.

Approximately 150 mg of the resulting spray dried sample of anamorelin monohydrochloride (or composition comprising anamorelin monohydrochloride) was accurately weighed out and dissolved in methanol (50 mL). Acetic acid (5 mL) and distilled water (5 mL) were added to the mixture. The resulting mixture was potentiometrically titrated using 0.01N silver nitrate and the endpoint was determined. A blank determination was also performed and correction was made, if necessary. The chloride content in the sample was calculated by the following formula. This measurement method of chloride content was performed without any cations other than proton ($H^+$).

Chloride content (%)=V×N×35.453×100×100/{W×[100−(water content (%))−(residual solvent (%))]}

V: volume at the endpoint (mL)
N: actual normality of 0.01 mol/L silver nitrate
35.453: atomic weight of Chlorine
W: weight of sample (mg)

TABLE 1A

| HCl (equivalent) | Chloride Content (wt. %) |
| --- | --- |
| 0.80 | 5.7 |
| 0.95 | 5.9 |
| 1.00 | 6.0 |
| 1.05 | 6.3 |

This data showed that anamorelin monohydrochloride produced by a fixed volume of HCl in water containing 0.80 or 1.05 molar equivalents of HCl relative to anamorelin free base had levels of chloride that were undesirable, and associated with product instability as shown in Example 3.

Alternatively, a fixed volume of HCl in water containing 0.95 moles of HCl relative to anamorelin free base was used to prepare anamorelin monohydrochloride (or composition comprising anamorelin monohydrochloride) as follows. Anamorelin free base (18.8 g, 34.4 mmol) and isopropyl acetate (341.8 g) were mixed in a 1000 mL flask. The mixture was heated at 40±5° C. to confirm dissolution of the crystals and then cooled at 25±5° C. Distilled water (22.3 g) and 3.6% diluted hydrochloric acid (33.1 g, 32.7 mmol, 0.95 equivalents) were added into the flask and washed with distilled water. After 30 minutes stirring, the reaction was static for more than 15 minutes and the lower layer (aqueous layer) was transferred into a separate 250 mL flask. Distilled water was added to the flask and concentrated under pressure at 50±+5° C. The resulting aqueous solution was then filtered and product isolated by spray drying to afford anamorelin monohydrochloride A (the present invention).

The physical properties of anamorelin monohydrochloride A were compared to anamorelin monohydrochloride produced by a traditional comparative method ("anamorelin monohydrochloride B") (comparative example). Anamorelin mono hydrochloride B in the comparative example was produced by bubbling HCl gas into isopropyl acetate to produce a 2M solution of HCl, and reacting 0.95 molar equivalents of the 2M HCl in isopropyl acetate with anamorelin free base. The physical properties of anamorelin monohydrochloride B are reported in Table 1B. This data shows that when 0.95 equivalents of HCl is added to anamorelin free base, the chloride content (or amount of anamorelin dihydrochloride) is increased, even when a stoichiometric ratio of hydrochloride to anamorelin of less than 1.0 is used, possibly due to uncontrolled precipitation. In addition, this data shows that the concentration of residual solvents in anamorelin monohydrochloride B was greater than the concentration in anamorelin monohydrochloride A.

TABLE 1B

| Anamorelin HCl Salt/Properties | HCl | Chloride Content (wt. %) | Residual Solvent Concentration (ppm) |
| --- | --- | --- | --- |
| A | mono | 5.9 | <1,000 |
| B | mono | 6.3 | 30,000-50,000 |

A similar decrease in residual solvent concentration was observed when 2-methyltetrahydrofuran was used as the dissolving solvent for anamorelin free base instead of isopropyl acetate in the process for preparing spray dried anamorelin monohydrochloride A (data not reported).

The residual solvent (organic volatile impurities) concentration (specifically isopropyl acetate) of anamorelin monohydrochloride in TABLE 1B was measured using gas chromatography (GC-2010, Shimadzu Corporation) according to the conditions shown in TABLE 1C.

TABLE 1C

| GAS CHROMATOGRAM CONDITIONS | |
| --- | --- |
| Detector | Flame ionization detector |
| Column | DB624 (length 30 m, i.d.0.32 mm, film thickness 1.8 μm, J&W) or equivalent |
| Carrier gas | Helium |
| Flow rate | 39 cm/sec (about 2.5 mL/min) |
| Column temperature | 40° C. (0-6 min) to (10° C./min) to 80° C. to (50° C./min) to 250° C. (13.425 min) |
| Injection temperature | 150° C. |
| Detector temperature | 260° C. |
| Make-up gas | Nitrogen 40 mL/min |
| Run duration | 11 min |
| HEAD SPACE CONDITIONS | |
| Oven temperature | 80° C. |
| Needle temperature | 130° C. |
| Transfer temperature | 140° C. |
| Equilibration time | 20 min |
| Pressurized time | 1.0 min |
| Drawing time | 1.0 min |
| Carrier gas pressure | 159 kPa |
| Injection time | 0.08 min |

Example 2. Spray Dry Methods

Several spray dry methods have been developed by varying the type of nozzle, the conditions at the nozzle, the inlet and outlet temperatures, the temperature of the condenser, and the feed rate. The amount of anamorelin monohydrochloride (or composition comprising anamorelin monohydrochloride) produced, the yield of each process and representative process parameters according to the present invention using Niro QSD-3.6 (trade mark, GEA process engineering Inc.) are reported in Table 2A.

TABLE 2A

| | Co-current nozzle | | | | | | Amount | |
| Batch | Ø [mm] | Flow [kg/h]/ P [bar] | T inlet [° C.] | T outlet [° C.] | T condenser [° C.] | Feed rate [kg/h] | of product [kg] | Yield |
| --- | --- | --- | --- | --- | --- | --- | --- | --- |
| 1 | 2 | 25 1.6 | 190 | 95 | 2 | 13.5 | 6.15 | 92.5% |
| A | 2 | 25 1.5 | 190 | 95 | 2 | 25 | 49.85 | 94.6% |
| B | 2 | 25 1.6 | 190 | 95 | 2 | 25 | 130.4 | 98.6% |

| | Rotary nozzle | | | | | | Amount | |
| Batch | P [bar] | Flow [kg/h] | T inlet | T outlet | T condenser | Feed rate | of product | Yield |
| --- | --- | --- | --- | --- | --- | --- | --- | --- |
| 2 | 3.3 | 10.1 | 190 | 95 | 2 | 13.5 | 6.12 | 98.5% |
| 3 | 4.4 | 13.6 | 190 | 95 | 2 | 13.5 | 5.97 | 99.2% |
| 4 | 5.0 | 15.6 | 190 | 95 | 2 | 13.5 | 6.39 | 97.8% |

Various physical properties of the anamorelin monohydrochloride (or composition comprising anamorelin monohydrochloride) prepared according to the foregoing examples were evaluated and reported below in Table 2B.

TABLE 2B

| | KF | Particle Size [μm] | | | Bulk density | Purity | Cl | OVI |
| Batch | [%] | D10 | D50 | D90 | [g/mL] | % | % | (ppm) |
| --- | --- | --- | --- | --- | --- | --- | --- | --- |
| 1 | 2.0 | 3.0 | 17.0 | 43.0 | 0.29 | 99.9 | 6.0 | <1000 |
| A | 2.0 | 4.2 | 16.0 | 40.6 | 0.29 | 100.0 | 6.0 | <1000 |
| B | 2.1 | 4.4 | 17.0 | 40.4 | 0.27 | 100.0 | 5.9 | <1000 |
| 2 | 2.1 | 1.6 | 22.3 | 52.4 | 0.32 | 99.9 | 6.0 | <1000 |
| 3 | 2.2 | 2.9 | 21.8 | 47.6 | 0.31 | 99.9 | 6.0 | <1000 |
| 4 | 2.2 | 4.4 | 24.7 | 52.5 | 0.32 | 99.9 | 6.0 | <1000 |

\* Purity determined by HPLC, and includes only related compounds.
\*\*OVI: Organic Volatile Impurities.

Similarly, the amount of anamorelin monohydrochloride (or a composition comprising anamorelin monohydrochloride) produced, the yield of each process and representative process parameters according to the present invention using Niro Mobile Minor (trade mark, GEA process engineering Inc.) were reported in Tables 2C and 2D.

TABLE 2C

| | Rotary nozzle | | | | Feed | Amount | |
| Batch | P [bar] | Flow [kg/h] | T inlet [° C.] | T outlet [° C.] | rate [kg/h] | of product [kg] | Yield |
| --- | --- | --- | --- | --- | --- | --- | --- |
| 1 | 2.8 | 80 | 188-192 | 83-87 | 3.3 | 26.0 | 98.6% |
| 2 | 2.8 | 80 | 188-192 | 83-87 | 3.3 | 23.0 | 98.4% |

TABLE 2D

| | KF | Particle Size [μm] | | | Purity | Cl | OVI |
| Batch | [%] | D10 | D50 | D90 | % | % | (ppm) |
| --- | --- | --- | --- | --- | --- | --- | --- |
| 1 | 2.4 | 6.4 | 16.8 | 33.6 | 99.9 | 6.1 | 173 |
| 2 | 2.5 | 7.3 | 19.8 | 38.6 | 100.0 | 6.0 | not detected |

As can be seen, anamorelin monohydrochloride (or a composition comprising anamorelin monohydrochloride) prepared by the method of present invention had desirable chloride content, reduced residual solvent and high purity when produced under a range of spray drying conditions.

Example 3. Stability Testing

The stability of anamorelin monohydrochloride (or composition comprising anamorelin monohydrochloride) prepared according to the foregoing examples was evaluated at 25° C./75% relative humidity and 40° C./75% relative humidity for one, three and six months. The purity of the anamorelin monohydrochloride (or composition comprising anamorelin monohydrochloride) was measured using high performance liquid chromatograph (HPLC) (Hewlett-Packard HP 1100 HPLC System, Agilent Technologies Inc.). The concentrated aqueous solution of anamorelin monohydrochloride A of example 1 was concentrated by spray drying using Niro QSD-3.6 (trade mark, GEA process engineering Inc.) to afford anamorelin monohydrochloride referred to as Batch A in Tables 2A and 2B) in an amorphous state. The resulting amorphous product was dissolved in acetonitrile: water (1:1) and measured under the conditions reported in Table 3A. The results are presented below in Table 3B. RRT refers to the relative retention time of the impurity versus anamorelin. In addition, the purity was converted into the amount of anamorelin free base within a sample without any other organic solvent since anamorelin monohydrochloride (or composition comprising anamorelin monohydrochloride) was dissolved in the solvent to be measured by HPLC condition.

TABLE 3A

| Detector | UV280 nm |
|---|---|
| Column | Zorbax Bonus RP (4.6 mm × 250 mm, 3.5 µm, Agilent) |
| Column temperature | 55° C. |
| Mobile phase | Mobile phase A: 0.1% Trifluoroacetic acid aqueous solution |
| | Mobile phase B: 0.1% Trifluoroacetic acid acetonitrile solution |

| Gradient | | |
|---|---|---|
| Time (min.) | Phase A (%) | Phase B (%) |
| 0 | 84 | 16 |
| 12 | 74 | 26 |
| 26 | 69.5 | 30.5 |
| 29 | 69.5 | 30.5 |
| 41 | 64 | 36 |
| 50 | 7 | 93 |
| 54 | 7 | 93 |
| 54.1 | 84 | 16 |
| 62 | 84 | 16 |

| Flow | 0.85 mL/min (retention time of anamorelin: 32 min) |
|---|---|
| run duration | 62 min |
| Injection volume | 10 µL |

TABLE 3B

| | month | anamorelin | Impurity 1 | Impurity 2 | Impurity 3 | Impurity 4 | Impurity 5 | Impurity 6 | Impurity 7 |
|---|---|---|---|---|---|---|---|---|---|
| Initial | | 100.0% | <0.05 | <0.05 | <0.05 | <0.05 | <0.05 | <0.05 | <0.05 |
| 25° C./60% RH | 1 | 100.0% | <0.05 | <0.05 | <0.05 | <0.05 | <0.05 | <0.05 | <0.05 |
| | 3 | 100.0% | <0.05 | <0.05 | <0.05 | <0.05 | <0.05 | <0.05 | <0.05 |
| | 6 | 100.0% | <0.05 | <0.05 | <0.05 | <0.05 | <0.05 | <0.05 | <0.05 |
| 40° C./75% RH | 1 | 100.0% | <0.05 | <0.05 | <0.05 | <0.05 | <0.05 | <0.05 | <0.05 |
| | 3 | 100.0% | <0.05 | <0.05 | <0.05 | <0.05 | <0.05 | <0.05 | <0.05 |
| | 6 | 100.0% | <0.05 | <0.05 | <0.05 | <0.05 | <0.05 | <0.05 | <0.05 |

As can be seen, the stability of the anamorelin monohydrochloride (or composition comprising anamorelin monohydrochloride) prepared according to the present invention was nearly unchanged, and high purity was maintained for six months under each set of conditions.

The long-term stability of three separate batches of anamorelin monohydrochloride (or composition comprising anamorelin monohydrochloride) having differing chloride contents were evaluated for stability at 25° C./60% relative humidity for one, two and three years, and 40° C./75% relative humidity for one, three and six months. The results are presented below in Table 3C. % Increase in Table 3C was calculated by the following formula.

% Increase = $(M-I)/I \times 100$

I: initial total impurity (%)

M: measured total impurity (%) at specific time (e.g., 3 months, 6 month and so forth)

TABLE 3C

| Initial Chloride Content | % Increase in Total Impurities From $T_0$ at 25° C./ 60% RH | | |
|---|---|---|---|
| (wt. %) | 1 Y | 2 Y | 3 Y |
| 6.2% | 85% | 114% | 100%. |
| 6.3% | 200% | 340% | 360% |
| 5.6% | 10% | 48% | 29% |
| 5.9% | 0% | 20% | 20% |

| | % Increase in Total Impurities From $T_0$ at 40° C./ 75% RH | | |
|---|---|---|---|
| | 1 M | 3 M | 6 M |
| 6.2% | 107% | 100% | 171% |
| 6.3% | 140% | 400% | 500% |
| 5.9% | 0% | 21% | 17% |

As can be seen, the long-term stability of the anamorelin monohydrochloride (or composition comprising anamorelin monohydrochloride) (from 5.3% to 6.3% chloride content) prepared according to the present invention was nearly unchanged, and high purity was maintained for three years under ambient storage conditions (25° C./60% RH).

Stability testing for anamorelin dihydrochloride relative to the monohydrochloride and anamorelin free base at 40° C./75% relative humidity is reported below in Table 3D. For the anamorelin dihydrochloride preparation, anamorelin free base was dissolved in ethyl acetate and a molar excess of hydrochloric acid in ethyl acetate was added into the mixture to precipitate anamorelin dihydrochloride. The resulting anamorelin dihydrochloride was filtered and dried (chloride content approximately 12.2%). HPLC Area % in Table 3D refers to the amount of converted value of anamorelin free base in samples.

As can be seen, the long-term stability of anamorelin dihydrochloride was easy to be changed relative to the monohydrochloride. Thus, when the content of anamorelin dihydrochloride in the composition is increased, the composition results in less stable.

TABLE 3D

| | Anamorelin Free Base | | | Anamorelin Mono-HCl | | | Anamorelin Di-HCl | | |
|---|---|---|---|---|---|---|---|---|---|
| | I.T. | 1 M | 3 M | I.T. | 1 M | 3 M | I.T. | 1 M | 3 M |
| HPLC Area % | 99.7% | 99.9% | 99.7% | 99.9% | 99.3% | 99.2% | 98.9% | 98.2% | 97.1% |

Example 4 Solubility Test

A solution of standard curve was prepared to 356 μmol/L by diluting standard substance (anamorelin free base (quantitative value: 93.90%), 86.6 mmol/L, isopropyl acetate solution) with acetonitrile. In addition, a sample solution was prepared according to the process that test compound (about 100 mg) added into distilled water (10.00 g), the solution was mixed for 10 minutes at 50° C. and then was placed overnight, obtained suspension was filtered by syringe with filter (0.2 μm) and the filtrate (48.93 mg) was diluted with acetonitrile (10 mL). A solution of standard curve and a sample solution (each 5 μL) were determined by injecting into HPLC (GULLIVER1500 HPLC system, JASCO Corporation). Since anamorelin monohydrochloride was completely dissolved in the 25% solution of anamorelin monohydrochloride (i.e., anamorelin monohydrochloride (Ig) was dissolved in distilled water (3 mL)), a solubility of anamorelin monohydrochloride was >333 mg/mL.

TABLE 4

| run | | solvent | mg/mL |
|---|---|---|---|
| 1 | anamorelin monohydrochloride | distilled water (initial pH 7) | >333 |
| 2 | Anamorelin free base | distilled water (initial pH 7) | 0.04 |

As can be seen, the solubility of the anamorelin monohydrochloride is superior to that of anamorelin free base in distilled water, illustrating that a reduction of chloride content in anamorelin monohydrochloride (or composition comprising anamorelin monohydrochloride) can lead to decreased solubility.

Example 5. Physical Characterization

Figure 2:
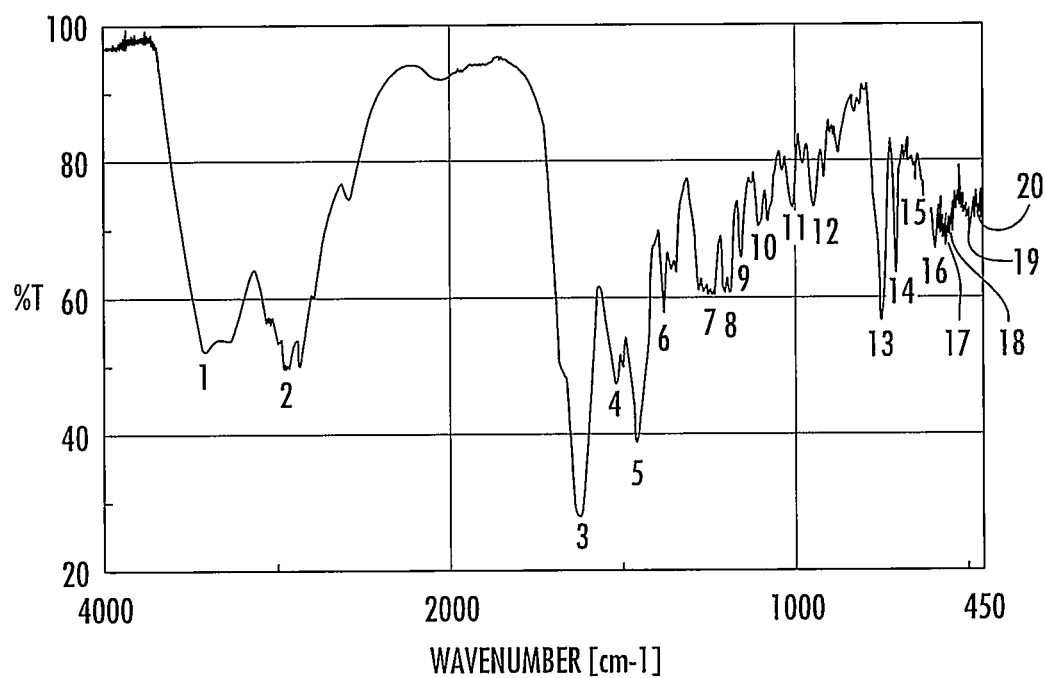
FIG. 2 is an infrared spectrum in KBr of amorphous anamorelin monohydrochloride or a composition comprising amorphous anamorelin monohydrochloride prepared according to the methods of the present invention.

The amorphous form of the anamorelin monohydrochloride (or composition comprising anamorelin monohydrochloride) produced by spray drying was evaluated using X-Ray powder diffraction and infrared resonance under the following measurement conditions. The XRPD spectra and IR spectra observed are depicted in FIGS. 1 and 2.

X-ray powder diffraction spectra Apparatus: BRUKER D8 DISCOVER with GADDS manufactured by BRUKER axs
  Target: Cu,
  Filter: None
  Voltage: 40 kV,
  Current: 40 mA,
  Light exposure: 5 min.
Infrared resonance spectrum
  Apparatus: FTIR-660 Plus produced by JASCO Corporation DURASCOPE produced by SENSIR Measuring method: Potassium bromide added into the tablet forming machine and it was pressured by hand-press to prepare the thin film. This sample was measured as background. Subsequently, the amorphous sample (1 mg) and potassium bromide (100 mg) was combined and the mixture added into the tablet forming machine to prepare the thin film and then measured.
  Dissolution performance: 2 cm$^{-1}$
  Scanning number of time: 16 times Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. Anamorelin monohydrochloride having a ratio of HCl to anamorelin of from 0.9:1 to 0.99:1.

2. Amorphous anamorelin monohydrochloride having a chloride content of from 5.6 to 6.3% and comprising less than 3% total impurities selected from by-products, contaminants, and degradation products.

3. Amorphous anamorelin monohydrochloride having a ratio of HCl to anamorelin of from 0.9:1 to 0.99:1.

4. The anamorelin monohydrochloride of claim 1, comprising less than 2% total impurities selected from by-products, contaminants, and degradation products.

5. The anamorelin monohydrochloride of claim 2, comprising less than 2% total impurities selected from by-products, contaminants, and degradation products.

6. The anamorelin monohydrochloride of claim 3, comprising less than 2% total impurities selected from by-products, contaminants, and degradation products.

7. The anamorelin monohydrochloride of claim 1, comprising less than 3% water.

8. The anamorelin monohydrochloride of claim 2, comprising less than 3% water.

9. The anamorelin monohydrochloride of claim 3, comprising less than 3% water.

10. The anamorelin monohydrochloride of claim 1 in an isolated state.

11. The anamorelin monohydrochloride of claim 2 in an isolated state.

12. The anamorelin monohydrochloride of claim 3 in an isolated state.

13. A pharmaceutical dosage form comprising the anamorelin monohydrochloride of claim 1 in combination with one or more pharmaceutically acceptable excipients.

14. A pharmaceutical dosage form comprising the anamorelin monohydrochloride of claim 2 in combination with one or more pharmaceutically acceptable excipients.

15. A pharmaceutical dosage form comprising the anamorelin monohydrochloride of claim 3 in combination with one or more pharmaceutically acceptable excipients.

16. A pharmaceutical dosage form comprising the anamorelin monohydrochloride of claim 1 in combination with one or more pharmaceutically acceptable excipients in the form a tablet or capsule or pellets or granules or powders.

17. A pharmaceutical dosage form comprising the anamorelin monohydrochloride of claim 2 in combination with one or more pharmaceutically acceptable excipients in the form a tablet or capsule or pellets or granules or powders.

18. A pharmaceutical dosage form comprising the anamorelin monohydrochloride of claim 3 in combination with one or more pharmaceutically acceptable excipients in the form a tablet or capsule or pellets or granules or powders.

19. The anamorelin monohydrochloride of claim 1 having a solubility in water greater than 333 mg/mL.

20. The anamorelin monohydrochloride of claim 2 having a solubility in water greater than 333 mg/mL.

21. The anamorelin monohydrochloride of claim 3 having a solubility in water greater than 333 mg/mL.

22. The anamorelin monohydrochloride of claim 1 having a stability defined by a percentage increase in impurities of no more than 114% when stored at 25° C. and a relative humidity of 60% for two years.

23. The anamorelin monohydrochloride of claim 2 having a stability defined by a percentage increase in impurities of no more than 114% when stored at 25° C. and a relative humidity of 60% for two years.

24. The anamorelin monohydrochloride of claim 3 having a stability defined by a percentage increase in impurities of no more than 114% when stored at 25° C. and a relative humidity of 60% for two years.

25. The anamorelin monohydrochloride of claim 2 having a chloride content of from 5.8 to 6.2%.

* * * * *